US009380994B2

(12) United States Patent
Seki et al.

(10) Patent No.: US 9,380,994 B2
(45) Date of Patent: Jul. 5, 2016

(54) ULTRASONIC DIAGNOSTIC APPARATUS

(75) Inventors: Takao Seki, Kanagawa (JP); Takao Suzuki, Kanagawa (JP); Hisashi Hagiwara, Kanagawa (JP); Yoshinao Tannaka, Kanagawa (JP); Yoshinobu Watanabe, Kanagawa (JP); Makoto Kato, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 1766 days.

(21) Appl. No.: 11/722,549

(22) PCT Filed: Dec. 19, 2005

(86) PCT No.: PCT/JP2005/023244
§ 371 (c)(1),
(2), (4) Date: Jun. 22, 2007

(87) PCT Pub. No.: WO2006/068079
PCT Pub. Date: Jun. 29, 2006

(65) Prior Publication Data
US 2008/0103392 A1 May 1, 2008

(30) Foreign Application Priority Data
Dec. 24, 2004 (JP) .................................. 2004-374227

(51) Int. Cl.
*A61B 8/00* (2006.01)
*A61B 8/08* (2006.01)

(52) U.S. Cl.
CPC .... *A61B 8/08* (2013.01); *A61B 8/44* (2013.01)

(58) Field of Classification Search
USPC ......... 600/455, 450, 449, 454, 457, 456, 463, 600/513–519
See application file for complete search history.

(56) References Cited

U.S. PATENT DOCUMENTS 5,163,434 A * 11/1992 Kumazawa ................... 600/455
5,224,480 A    7/1993 Yamada et al.
5,622,174 A * 4/1997 Yamazaki ..................... 600/441

(Continued)

FOREIGN PATENT DOCUMENTS

JP        04-035653        2/1992
JP        08-080299        3/1996

(Continued)

OTHER PUBLICATIONS

International Search Report for corresponding Application No. PCT/JP2005/023244 mailed Feb. 21, 2006.

(Continued)

*Primary Examiner* — Joel F Brutus
(74) *Attorney, Agent, or Firm* — Lucas & Mercanti, LLP

(57) ABSTRACT

An ultrasonic diagnostic apparatus according to the present invention includes: a transmitting section, which drives a probe that transmits an ultrasonic wave toward a subject; a receiving section, which receives an ultrasonic echo, produced by getting the ultrasonic wave reflected by the subject, through the probe, thereby generating a received signal; a property value calculating section for calculating property values of the subject based on the received signal over a period of time; a stability estimating section for sequentially estimating the degrees of stability of the property values that have been calculated over the period of time; and a presenting section for presenting the degrees of stability thereon.

11 Claims, 5 Drawing Sheets

(56) References Cited

U.S. PATENT DOCUMENTS

| | | | |
|---|---|---|---|
| 5,840,028 A | 11/1998 | Chubachi et al. | |
| 6,415,166 B1* | 7/2002 | Van Hoy et al. | 600/323 |
| 6,527,717 B1* | 3/2003 | Jackson et al. | 600/437 |
| 6,957,398 B1* | 10/2005 | Nayeri | 715/867 |
| 2003/0120152 A1* | 6/2003 | Omiya | 600/443 |
| 2003/0171668 A1* | 9/2003 | Tsujino et al. | 600/407 |
| 2004/0159155 A1* | 8/2004 | Ogasawara | 73/633 |
| 2007/0036588 A1* | 2/2007 | Momose | 399/182 |

FOREIGN PATENT DOCUMENTS

| | | |
|---|---|---|
| JP | 10-005226 | 1/1998 |
| JP | 11-128227 | 5/1999 |
| JP | 2000-229078 | 8/2000 |

OTHER PUBLICATIONS

Form PCT/ISA/237 and a partial English translation.

\* cited by examiner (a)          (b)

US 9,380,994 B2

ULTRASONIC DIAGNOSTIC APPARATUS

TECHNICAL FIELD

The present invention relates to an ultrasonic diagnostic apparatus for inspecting a subject's internal tissue and more particularly relates to an ultrasonic diagnostic apparatus for estimating subject's attribute property values.

BACKGROUND ART

An ultrasonic diagnostic apparatus is used to make a non-invasive checkup on a subject by irradiating him or her with an ultrasonic wave and analyzing the information contained in its echo signal. For example, a conventional ultrasonic diagnostic apparatus that has been used extensively converts the intensity of an echo signal into its associated pixel luminance, thereby presenting the subject's structure as a tomographic image. In this manner, the internal structure of the subject can be known.

Meanwhile, some people are attempting recently to track the motion of a subject's tissue more precisely and evaluate the strain and the elasticity, viscosity or any other physical (attribute) property of the tissue mainly by analyzing the phase of the echo signal.

Patent Document No. 1 discloses a method for tracking a subject's tissue highly precisely by calculating the magnitude of instantaneous displacement of a local region of the subject based on the phase difference of an ultrasonic echo signal to be transmitted and received at regular intervals and by summing the magnitudes of displacements together.

Patent Document No. 2 further develops the method of Patent Document No. 1 into a method of calculating the elasticity of a subject's tissue (e.g., an arterial vascular wall, in particular). According to this method, first, an ultrasonic wave is transmitted from a probe 101 toward a vascular 411 as shown in FIG. 8(a). And the echo signals, reflected from measuring points A and B on the vascular wall, are analyzed by the method of Patent Document No. 1, thereby tracking the motions of the measuring points A and B. FIG. 8(b) shows the tracking waveforms TA and TB showing the locations of the measuring points A and B along with an electrocardiographic complex ECG.

As shown in FIG. 8(b), the tracking waveforms TA and TB have the same periodicity as the electrocardiographic complex ECG, which shows that the artery dilates and shrinks in sync with the cardiac cycle of the heart. More specifically, when the electrocardiographic complex ECG has outstanding peaks called "R waves", the heart starts to shrink, thus pouring blood flow into the artery. As a result, the vascular wall is dilated rapidly. That is why soon after the R wave has appeared on the electrocardiographic complex ECG, the tracking waveforms TA and TB rise steeply and the artery dilates rapidly. After that, however, as the heart dilates slowly, the tracking waveforms TA and TB gradually fall to their original levels and the artery shrinks gently. The artery repeats such a motion cyclically.

The difference between the tracking waveforms TA and TB is represented as a waveform W showing a variation in thickness between the measuring points A and B. Supposing the variation of the thickness variation waveform is $\Delta W$ and the reference thickness between the measuring points A and B during initialization is Ws, the magnitude of strain $\epsilon$ between the measuring points A and B is calculated by:

$$\epsilon = \Delta W / Ws$$

The elasticity Er between the measuring points A and B is given by:

$$Er = \Delta P/\epsilon = \Delta P \cdot Ws / \Delta W$$

where $\Delta P$ is the blood pressure difference at this time.

Therefore, by measuring the elasticity Er for multiple spots on a tomographic image, an image representing the distribution of elasticities can be obtained. If an atheroma 412 has been created in the vascular wall as shown in FIG. 8(a), the atheroma 412 and its surrounding vascular wall tissue have different elasticities. That is why if an image representing the distribution of elasticities is obtained, it can be determined whether an atheroma has been created or not or where the atheroma is located.

Patent Document No. 1: Japanese Patent Application Laid-Open Publication No. 10-5226
Patent Document No. 2: Japanese Patent Application Laid-Open Publication No. 2000-229078

DISCLOSURE OF INVENTION

Problems to be Solved by the Invention

When inspecting a subject using such an ultrasonic diagnostic apparatus, the operator gets an ultrasonic wave transmitted and received by bringing the probe into contact with the subject's body. Thus, the probe may shift easily from the observation spot due to the inconstant movement of the operator's hand or the subject's body. A property value such as the elasticity, in particular, is measured by sensing a very small displacement of the subject's internal tissue as described above. That is why if the relative position of the probe to the spot of observation on the subject has varied, a proper property value could not be obtained anymore.

As far as a tomographic image is concerned, the unwanted movement of the operator's hand or the subject's body can be easily sensed because a clear image could not be obtained in that case. As for the property value obtained as a numerical value, however, it would be much more difficult to determine whether the unusual property value has resulted from the inconstant movement of the operator's hand or the subject's body or some disease of the tissue under observation.

In order to overcome the problems described above, the present invention has an object of providing an ultrasonic diagnostic apparatus that can present the degree of stability of a property value measured while a subject is being inspected.

Means for Solving the Problems

An ultrasonic diagnostic apparatus according to the present invention includes: a transmitting section, which drives a probe that transmits an ultrasonic wave toward a subject; a receiving section, which receives an ultrasonic echo, produced by getting the ultrasonic wave reflected by the subject, through the probe, thereby generating a received signal; a property value calculating section for calculating property values of the subject based on the received signal over a period of time; a stability estimating section for sequentially estimating the degrees of stability of the property values that have been calculated over the period of time; and a presenting section for presenting the degrees of stability thereon.

In one preferred embodiment, the stability estimating section calculates either the variance or the standard deviation of a plurality of property values that have been calculated over the period of time at a predetermined spot of interest, or in a predetermined region of interest, of the subject, and estimates the degree of stability based on the variance or the standard deviation.

In this particular preferred embodiment, the presenting section is a display device, which presents an image that has been generated so as to represent the degree of stability.

In a specific preferred embodiment, the stability estimating section further generates rating images representing the degrees of stability and the presenting section presents the rating images thereon.

In a more specific preferred embodiment, the stability estimating section further generates an image representing the maximum value of the degrees of stability that have been calculated sequentially and the presenting section presents the image representing the maximum value.

In another preferred embodiment, the ultrasonic diagnostic apparatus further includes: a tomographic image processing section for generating a tomographic image of the subject based on the received signal; a property value image processing section for generating a property value image representing the distribution of property values based on the property values; and an image synthesizing section, which receives biomedical information of the subject and synthesizes the biomedical information, the tomographic image and the property value image together, thereby generating data for a synthetic image to be presented on the presenting section. The image synthesizing section receives the degree of stability from the stability estimating section and changes the modes of presentation of at least one of the biomedical information, the tomographic image and the property value image according to the degree of stability.

In still another preferred embodiment, the image synthesizing section synthesizes the tomographic image and the property value image together such that corresponding spots of interest agree with each other, and changes the degrees of transparency of the tomographic image or the property value image according to the degree of stability when the two images are superposed one upon the other.

In yet another preferred embodiment, the biomedical information is an electrocardiogram of the subject, and the image synthesizing section changes the modes of presentation of the electrocardiogram according to the degree of stability.

In yet another preferred embodiment, the ultrasonic diagnostic apparatus further includes an image memory section for storing the data of the synthetic image generated by the image synthesizing section in association with the degree of stability. The image synthesizing section gets the synthetic image data from the image memory section and outputs only synthetic image data, of which the degree of stability exceeds a predetermined threshold value, to the display section.

In yet another preferred embodiment, the presenting section is an acoustic transducer and transforms an electrical signal, which has been generated based on the degree of stability, into a sound.

Effects of the Invention

According to the present invention, the degree of stability of a property value, which has been obtained during observation, can be known. That is why a highly reliable diagnosis can be made by using the ultrasonic diagnostic apparatus of the present invention.

Figure 1:
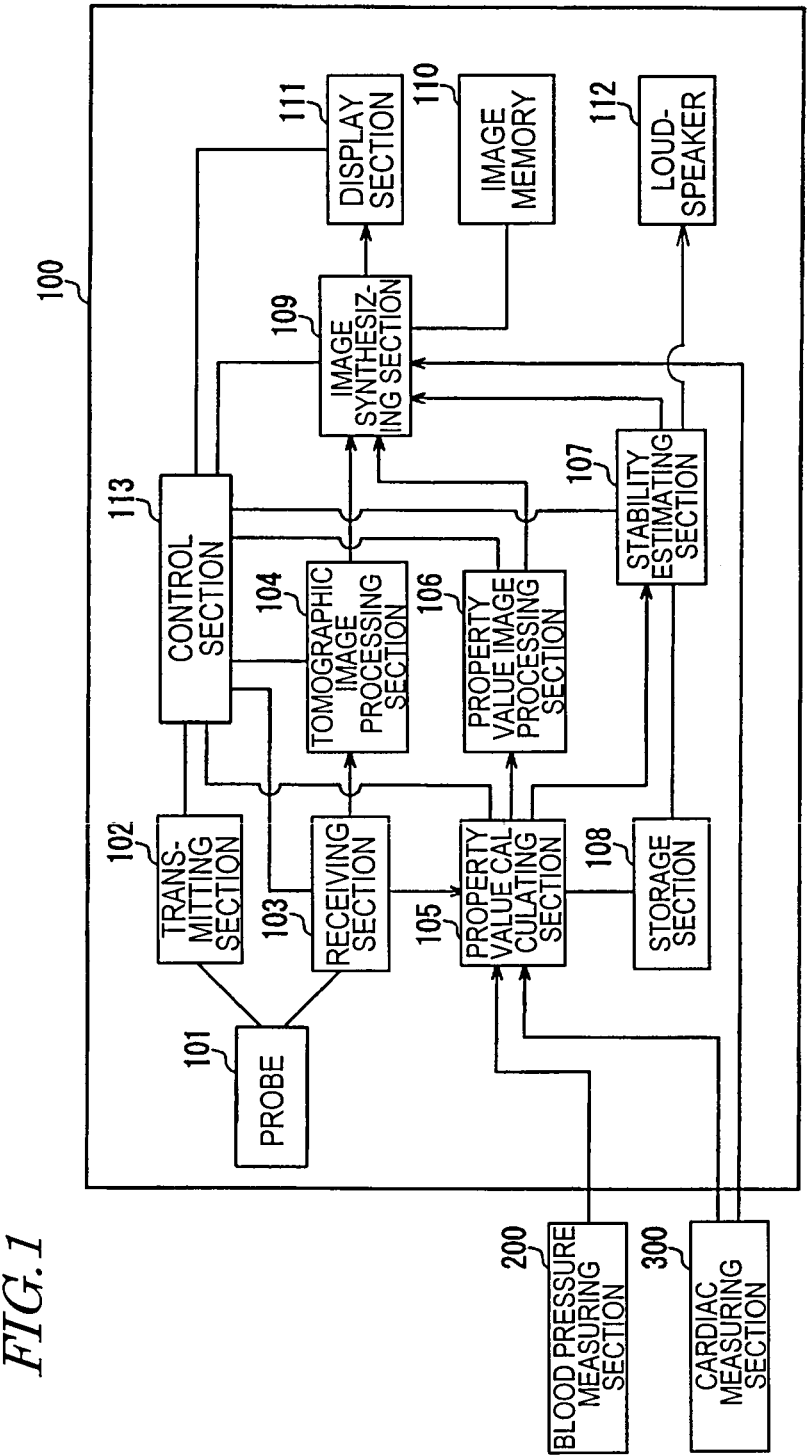
FIG. 1 is a block diagram showing a configuration for an ultrasonic diagnostic apparatus according to a first preferred embodiment of the present invention.

DESCRIPTION OF REFERENCE NUMERALS 100 ultrasonic diagnostic apparatus
101 probe
102 transmitting section
103 receiving section
104 tomographic image processing section
105 property value calculating section
106 property value image processing section
107 stability estimating section
108 storage section
109 image synthesizing section
110 image memory
111 display section
112 loudspeaker
113 control section
200 blood pressure measuring section
300 cardiac measuring section

BEST MODE FOR CARRYING OUT THE INVENTION

Hereinafter, preferred embodiments of an ultrasonic diagnostic apparatus according to the present invention will be described in detail with reference to the accompanying drawings. In the following specific example, the operator measures the elasticity of a subject's region of interest by bringing a probe into contact with the surface of that region. However, the elasticity is just one of various property values. And the magnitude of strain, viscosity or any other value representing an attribute property of the subject's tissue in question may be measured using this ultrasonic diagnostic apparatus.

Embodiment 1

FIG. 1 is a block diagram showing a configuration for an ultrasonic diagnostic apparatus according to a first preferred embodiment of the present invention. As Shown in FIG. 1, the ultrasonic diagnostic apparatus 100 includes a probe 101, a transmitting section 102, a receiving section 103, a tomographic image processing section 104, a property value calculating section 105, a property value image processing section 106, a stability estimating section 107, a storage section 108, an image synthesizing section 109, an image memory 110, a display section 111 and a loudspeaker 112. A blood pressure measuring section 200 and a cardiac measuring section 300 are also connected to the ultrasonic diagnostic apparatus 100. In this preferred embodiment, the ultrasonic diagnostic apparatus 100 is supposed to include the probe 101. However, the ultrasonic diagnostic apparatus 100 may also be designed so as to have no probe 101 but be connectable to any probe currently available.

The ultrasonic diagnostic apparatus 100 further includes a control section 113 for controlling all of these components. The control section 113 may be implemented as a microcomputer, for example, and includes an input interface (not shown) for an input device such as a mouse, a keyboard, a push button, or a dial. By operating any of these input devices, the operator can enter his or her instruction or information on how the ultrasonic diagnostic apparatus 100 should operate. For example, by tapping a key (such as a freeze key), the operator can switch the modes of operation between a live mode and a cine mode. As used herein, the "live mode" refers to a mode of operation in which while measuring is done with ultrasonic waves, the results of the measurements are shown on the display section 111 in real time. On the other hand, the "cine mode" refers to a mode of operation in which measurement data that was collected in the past and has been stored in the image memory 110 is read out from the memory 110 and presented on the display section 111. Also, as will be described in detail later, the operator may also decide, by operating the input device, whether the degree of stability of the property value should be presented audibly or visually. Optionally, he or she may even select both of these two types of presentations.

In accordance with the instruction given by the control section 113, the transmitting section 102 generates a drive pulse signal that drives the probe 101. The probe 101 converts the drive pulse signal that has been generated by the transmitting section 102 into an ultrasonic pulse and sends out the ultrasonic pulse toward a subject. The drive pulse signals are generated continuously at regular time intervals.

The ultrasonic echo, produced by getting the ultrasonic pulse reflected by an internal organ of the subject, is converted by the probe 101 into an electrical signal. The receiving section 103 receives the ultrasonic echo at the probe 101 and amplifies the converted electrical signal, thereby generating a received signal.

The probe 101 consists of multiple piezoelectric transducers (not shown). The time delays of the drive pulse signals, generated by the transmitting section 102 and to be applied to the piezoelectric transducers, and the received signals, received at those piezoelectric transducers and then generated by the receiving section 103, are controlled by a time delay control section (not shown). In this manner, the acoustic line direction and depth of focus of each ultrasonic pulse transmitted from the probe 101 are adjusted. Optionally, only a received signal representing an echo that has been reflected from a particular direction or position can be detected.

The tomographic image processing section 104 includes a band-pass filter, a logarithmic amplifier, a detector, and other components, and generates tomographic image data, representing the internal structure of the subject, based on the received signal supplied from the receiving section 103. The tomographic image data, generated by the tomographic image processing section 104, is output to the image synthesizing section 109. Responsive to every new received signal, the tomographic image processing section 104 generates the image data.

The property value calculating section 105 calculates, based on the received signal, the magnitudes of strain caused in respective portions of the subject's tissue due to a variation in blood pressure by the strain factor calculating method to be described later. Also, based on the magnitude of strain and the blood pressure value obtained by the blood pressure measuring section 200, the property value calculating section 105 calculates the elasticity of the subject's tissue by the elasticity calculating method to be described later, too. The magnitude of strain and elasticity are calculated over a period of time every cardiac cycle of the subject. For that purpose, the property value calculating section 105 receives the subject's biomedical information (e.g., information about his or her cardiac cycle among other things) from the cardiac measuring section 300, including an electrocardiograph and a phonocardiograph, and uses it as a trigger for calculating the magnitude of strain and elasticity. The elasticity calculated by the property value calculating section 105 is output to the property value image processing section 106, the stability estimating section 107 and the storage section 108. The storage section 108 may be implemented as a memory, for example.

Based on the elasticities calculated by the property value calculating section 105, the property value image processing section 106 generates a two-dimensional distribution of elasticities on the same profile as the tomographic image data. Then, the property value image processing section 106 outputs the distribution as elasticity image data to the image synthesizing section 109. Since the elasticity is calculated every cardiac cycle, the two-dimensional elasticity distribution is also calculated every cardiac cycle.

The stability estimating section 107 gets the elasticity values, which have been calculated by the property value calculating section 105 over a period of time, and estimates the degree of stability of the elasticities. Specifically, the stability estimating section 107 figures out the degree of stability of the elasticities based on the variance or standard deviation of the elasticities that were calculated a number of times in the same spot or region of interest and that have been stored in the storage section 108. The elasticities, of which the degree of stability should be estimated, may or may not be continuous with each other on the time axis. In this preferred embodiment, the stability estimating section 107 further generates, based on the degree of stability estimated, audio or visual diagnostic data showing the degree of stability.

The image synthesizing section 109 gets the tomographic image data from the tomographic image processing section 104, the elasticity image data from the property value image processing section 106, and the biomedical information, such as an electrocardiogram and a phonocardiogram, from the cardiac measuring section 300, respectively, and synthesizes all of these data together, thereby generating image output data. In this case, the image synthesizing section 109 is also notified of the degree of stability of elasticities by the stability estimating section 107 and changes at least one of the tomographic image, the elasticity image and the biomedical information according to the degree of stability provided. If the stability estimating section 107 generates the rating image data showing the degree of stability, not just the tomographic image data, the elasticity image data, and the biomedical information but also that rating image data showing the degree of stability are synthesized together.

The image memory 110 stores the image output data generated as synthetic data by the image synthesizing section 109. In this case, the image output data may be stored in association with the degrees of stability. The image output data stored may be used in a cine mode, for example, so as to be presented and shown continuously on the display section 111.

The display section 111 may be a monitor to present the image output data supplied from the image synthesizing section 109. The display section 111 may also present an arbitrary frame or a number of consecutive image output data that have been read by the image synthesizing section 109 from the image memory 110. On the synthetic image presented on the display section 111, at least one of the tomographic image, the elasticity image and the biomedical information changes according to the degree of stability. Or the rating image showing the degree of stability may be included in the synthetic image presented on the display section 111. That is why the display section 111 may be regarded as presenting the degree of stability that has been estimated by the stability estimating section 107.

If the stability estimating section 107 generates audio diagnostic data showing the degree of stability, then the loudspeaker 112, which is an acoustic transducer, may transduce the audio data into a sound representing the degree of stability. The loudspeaker may be replaced with any other acoustic transducer such as a piezoelectric buzzer.

Hereinafter, it will be described how this ultrasonic diagnostic apparatus 100 operates. While the ultrasonic diagnostic apparatus 100 is operating, the blood pressure measuring section 200 senses a variation in subject's blood pressure and the cardiac measuring section 300 takes an electrocardiogram (or a phonocardiogram) of the subject.

First, the operator decides, by handling an input device, whether he or she'd like to have the degree of stability of elasticities presented audibly or visually. Optionally, the degree of stability may be presented both audibly and visually. Next, various measuring conditions, including the duration of ultrasonic pulses, are entered into the ultrasonic diagnostic apparatus 100 through the input device and the probe 101 is brought into contact with the subject.

In accordance with the instruction entered by the user, the control section 113 instructs the transmitting section 102 to generate a drive pulse signal. In response, the probe 101 transforms the drive pulse signal into an ultrasonic pulse and radiates the pulse toward the subject. The ultrasonic pulse is reflected by the internal tissue of the subject to produce an ultrasonic echo, which soon reaches the probe 101. Then, the probe 101 transforms the received ultrasonic echo into an electrical signal and passes the signal to the receiving section 103, which amplifies the electrical signal received from the probe 101, thereby generating a received signal. The received signal is then output to the tomographic image processing section 104 and the property value calculating section 105.

The tomographic image processing section 104 generates image data, representing a tomographic image of the subject's internal tissue, by mapping the amplitude of the received signal to a luminance, for example.

The property value calculating section 105 calculates the elasticity based on the received signal. More specifically, as disclosed in Patent Documents Nos. 1 and 2, for example, under the restriction that two signals received at a very short interval have the same amplitude but varied phases and reflected points, the phase difference is calculated by a minimum square method so as to minimize the magnitude of matching error between the waveforms of the two received signals. The motion velocity of the measuring point that has been set on the subject is figured out based on this phase difference and then those differences are integrated together, thereby plotting a waveform representing the displacements of the measuring point. The difference between the waveforms representing the displacements of two measuring points is a waveform representing the variation in the thickness of the tissue interposed between the two measuring points. Since the measuring points are set two-dimensionally on the tomographic image, the tissue, of which the thickness variation should be figured out, is also arranged two-dimensionally. Using the initial value, maximum thickness and minimum thickness of the thickness variation waveform, the property value calculating section 105 calculates the magnitude of strain caused in the subject's tissue due to a variation in blood pressure by the following Equation (1):

$$\text{Magnitude of strain} = ((\text{maximum thickness}) - (\text{minimum thickness}))/(\text{initial thickness}) \qquad (1)$$

Furthermore, using the magnitude of strain calculated by Equation (1) and the variation in blood pressure measured by the blood pressure measuring section 200, the property value calculating section 105 figures out the elasticity of the subject's tissue by the following Equation (2):

$$\text{Elasticity} = ((\text{maximum blood pressure}) - (\text{minimum blood pressure}))/(\text{magnitude of strain}) \qquad (2)$$

For example, suppose the maximum blood pressure is 120 mmHg, the minimum blood pressure is 80 mmHg (i.e., the pulse pressure is 40 mmHg), the maximum and minimum thicknesses at an arbitrary spot on the blood vessel wall are 80 μm and 70 μm, respectively, and the thickness of the blood vessel wall has an initial value of 80 μm. In that case, the magnitude of strain of the subject's tissue is 0.125 (=(80−70)/80) and the elasticity is 320 (=(120−80)/0.125).

The magnitude of strain and elasticity are calculated and updated every cardiac cycle. The property value calculating section 105 outputs the elasticity thus obtained to the stability estimating section 107, the property value image processing section 106 and the storage section 108.

The stability estimating section 107 sequentially obtains the degrees of stability of elasticities as variances of elasticities that have been calculated sequentially at a predetermined spot of interest or region of interest. The latest elasticity may be received directly from the property value calculating section 105, while the other earlier elasticities are stored in the storage section 108. Thus, the stability estimating section 107 gets the elasticity data from the storage section 108.

Hereinafter, a method for estimating the degree of stability of elasticity will be described for a typical situation where the elasticity at an arbitrary spot is measured five times in total (i.e., through the first through fifth measurements). The following Table 1 shows exemplary elasticities that were measured at the arbitrary spot:

TABLE 1

|  | Elasticity | Difference from average | Squared difference |
|---|---|---|---|
| $1^{st}$ | 320 | 3 | 9 |
| $2^{nd}$ | 300 | −17 | 289 |
| $3^{rd}$ | 320 | 3 | 9 |
| $4^{th}$ | 330 | 13 | 169 |
| $5^{th}$ | 315 | −2 | 4 |

First, the stability estimating section 107 works out the average of the five elasticities shown in Table 1. Since the sum of the five elasticities is 1,585, the average of the elasticities is 317. Next, the stability estimating section 107 calculates the difference between each elasticity and the average elasticity (see the "difference from average" shown in Table 1), and then calculates the square of the difference between each elasticity and the average elasticity (see the "squared difference" in FIG. 2). Then, the average of the squared differences between the elasticities and the average elasticity is worked out, which is the variance to calculate (that is 96 in this example).

Then, the stability estimating section 107 compares the variance to the threshold value of the degrees of stability of elasticities. Suppose the degrees of stability of elasticities have a threshold value of 100, for example. In that case, since the variance calculated by the stability estimating section 107 is 96, which is less than 100, the degree of stability of elasticity at the arbitrary spot is estimated to be high.

Optionally, two or more threshold values may be set. Then, the degree of stability would be rated according to the threshold values set. Alternatively, either the variance value or a value obtained by multiplying its inverse number by an appropriate constant may be used as the degree of stability without setting any threshold value.

New elasticity is calculated by the property value calculating section 105 every cardiac cycle. That is why the stability estimating section 107 figures out the variance by making those calculations on the five latest elasticities. If the inconstant movement of the operator's hand or the subject's body is significant, then the elasticity will make a big difference and the resultant variance will also increase. If the movement of the hand or the body decreases, however, the elasticity will hardly change and the variance will decrease. That is to say, the degree of stability rises.

In the example described above, the degree of stability is supposed to be calculated based on the elasticities that have been obtained at an arbitrary spot. However, the degree of stability of elasticity does not have to be calculated at one arbitrary spot. Alternatively, the degree of stability of elasticities may also be calculated on a region, including a plurality of arbitrary spots, as described above. In that case, the stability estimating section 107 calculates the variances of elasticities that have been sequentially obtained at multiple spots included in the region of interest and works out the average of those variances as the degree of stability. Alternatively, the stability estimating section 107 may also work out the degree of stability as the variance of average elasticities that have been calculated at multiple spots in a region of interest.

Furthermore, the preset threshold value of the degree of stability of elasticities is not limited to the value described above, either. The threshold value of the degree of stability just needs to be determined by either the magnitudes of the elasticities or the number of elasticity values that were calculated in the past and are stored in the storage section 108.

If the operator has selected, by handling the input device, a mode in which the degree of stability of elasticity is presented audibly (i.e., as a sound), then the stability estimating section 107 generates audio data representing the degree of stability. For example, if the degree of stability is low, audio data with a high frequency may be generated. On the other hand, if the degree of stability is high, audio data with a low frequency may be generated. However, this is just an example and the audio data only needs to vary according to the degree of stability. For instance, data representing a clear sound may be generated if the degree of stability is high and data representing an unclear sound may be generated if the degree of stability is low. Alternatively, data representing a consonance may be generated if the degree of stability is high and data representing a dissonance may be generated if the degree of stability is low. Still alternatively, a prerecorded human voice may also be used. In any case, the audio data generated is supplied to the loudspeaker 112, which converts the data into a sound.

On the other hand, if the operator has selected a mode in which the degree of stability of elasticity is presented visually, then the stability estimating section 107 generates image data representing the degree of stability. Such image data will be described in detail later.

The property value image processing section 106 receives the elasticities that have been calculated by the property value calculating section 105 and plots the distribution of elasticities to be superimposed on a tomographic image, which will be generated by the tomographic image processing section 104 to represent the subject's tissue. The distribution of elasticities thus obtained is supplied as elasticity image data to the image synthesizing section 109.

The storage section 108 receives the elasticity values that have been calculated by the property value calculating section 105. Specifically, the elasticities in the entire range of the elasticity distribution to be plotted by the property value image processing section 106 are received by, and immediately stored in, the storage section 108. It should be noted that the elasticities do not have to be stored in the storage section 108 only at this timing. Optionally, every time an elasticity value is calculated by the property value calculating section 105, the value may be stored in the storage section 108.

The image synthesizing section 109 superposes the tomographic image data supplied from the tomographic image processing section 104 and the elasticity image data supplied from the property value image processing section 106 one upon the other such that their spots of interest agree with each other, thereby synthesizing the tomographic image data and the elasticity image data together. In addition, the image synthesizing section 109 further gets the electrocardiogram (or phonocardiogram) from the cardiac measuring section 300 and synthesizes it with the two types of data, too.

If the operator has selected the mode in which the degree of stability of elasticity is presented visually, the image synthesizing section 109 also synthesizes diagnostic data, showing the degree of stability, with the other types of data. In any case, the resultant synthetic image data is output to the display section 111 and is stored in the image memory 110, too.

Figure 2:
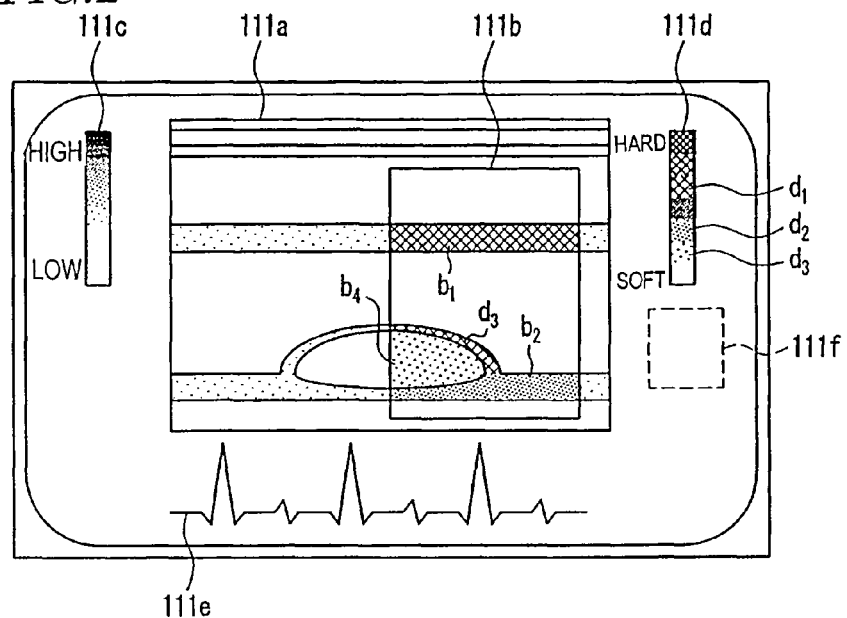
FIG. 2 shows an example of an image presented on the display section 111 of the ultrasonic diagnostic apparatus shown in FIG. 1.

FIG. 2 illustrates an exemplary mode of display on the display section 111 of the ultrasonic diagnostic apparatus 100. In FIG. 2, a tomographic image of the blood vessel is presented in B mode as an example.

As shown in FIG. 2, the image presented on the display section 111 includes a tomographic image 111a, an elasticity image 111b, a reflection intensity scale 111c, an elasticity scale 111d, a biomedical information (e.g., electrocardiogram or phonocardiogram) display area 111e and a degree of stability display area 111f.

The tomographic image 111a represents a blood vessel. The reflection intensity scale 111c represents the intensity of the reflected echo, which has been received at the receiving section 103, at multiple reflection intensity levels with a number of different colors or luminances. Likewise, each part of the tomographic image 111a is also shown in the color or luminance of its associated intensity of the reflected echo that has been received at the receiving section 103.

The elasticity image 111b shows the elasticity distribution on the blood vessel wall and is superposed on the tomographic image 111a. The elasticity scale 111d shows multiple elasticity levels in a number of different colors. The blood vessel wall portions b1 through b4 of the elasticity image 111b are shown in respective colors representing their elasticity values that have been calculated by the property value calculating section 105. Specifically, in this example, the blood vessel portions b1 and b3 are at elasticity level d1, which shows that their tissue is relatively hard, while the blood vessel portions b2 and b4 are at elasticity levels d2 and d3, respectively, which shows their tissue is relatively soft.

It should be noted that if the elasticity image 111b is shown in multiple colors on the display section 111, then the tomographic image 111a is preferably presented as a monochrome image (i.e., in gray scales) to clarify what data is emphasized.

In the electrocardiogram or phonocardiogram display area 111e, the electrocardiogram or phonocardiogram, supplied from the cardiac measuring section 300, is presented. And in the degree of stability display area 111f, presented is a rating image that has been generated by the stability estimating section 107 to show the degree of stability.

Hereinafter, specific exemplary images, representing the degrees of stability of elasticity in the degree of stability display area 111f, will be described. The degree of stability may always be presented in one of the following four modes of presentation. Alternatively, the degree of stability may also be presented selectively in any of those four modes at the operator's instruction that has been entered with the input device.

First Mode of Presentation

Figure 3:
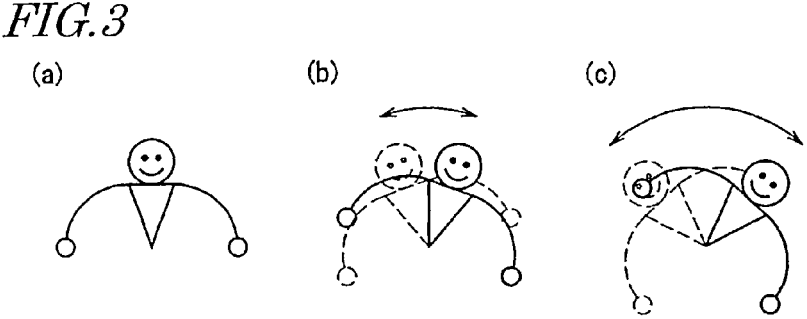
FIG. 3(a) illustrates an image representing a situation where the elasticity is completely stabilized.
FIG. 3(b) illustrates an image representing a situation where the elasticity has a relatively high degree of stability.
FIG. 3(c) illustrates an image representing a situation where the elasticity has a relatively low degree of stability.

In this exemplary mode of presentation, the degree of stability of elasticity is presented using a pendulum type image as shown in FIG. 3. Specifically, FIG. 3(a) illustrates how the pendulum image may look in a situation where the elasticity is completely stabilized. FIG. 3(b) illustrates how the pendulum may look in a situation where the degree of stability of elasticity is relatively high. And FIG. 3(c) illustrates how the pendulum may look in a situation where the degree of stability of elasticity is relatively low.

As shown in FIGS. 3(a) through 3(c), the amplitude of swing of the pendulum image represents the degree of stability of elasticity. That is to say, the smaller the amplitude of swing of the pendulum, the higher the degree of stability of elasticity. In other words, the greater the amplitude of swing of the pendulum, the lower the degree of stability of elasticity. The stability estimating section 107 may set two threshold values and compare the variance calculated to the two threshold values, thereby generating one of three types of image data shown in FIGS. 3(a) through 3(c) according to the degree of stability. Alternatively, image data representing a pendulum that increases its amplitude of swing either continuously or stepwise according to the variance value calculated may also be generated without setting any threshold value.

Second Mode of Presentation

Figure 4:
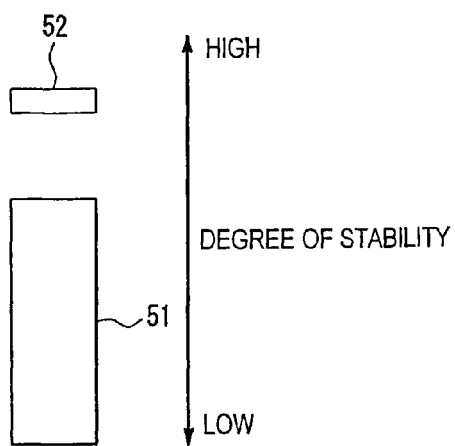
FIG. 4 is an exemplary rating image presenting the degree of stability as a sort of bar graph.

In this exemplary mode of presentation, the degree of stability of elasticity is presented using a bar graph type image as shown in FIG. 4, which illustrates an exemplary bar graph type rating image.

As shown in FIG. 4, the bar graph type rating image 51 presents the degree of stability that has been calculated by the stability estimating section 107. Specifically, the taller the bar graph type rating image 51, the higher the degree of stability of elasticity. In other words, the shorter the bar graph type rating image 51, the lower the degree of stability of elasticity. In any case, the height of the rating image 51 is determined by the variance value that has been calculated by the stability estimating section 107.

The line 52 indicates the highest degree of stability of elasticity that has ever been calculated. The image synthesizing section 109 includes a memory (not shown), which stores that highest degree of stability (maximum degree of stability). By reference to the actual value of the maximum degree of stability, the image synthesizing section 109 determines the presentation location of the line 52 with respect to the bar graph type rating image 51.

The degree of stability of elasticity that has been calculated by the stability estimating section 107 is compared to the maximum degree of stability stored in the memory. And the greater one of these two values is newly stored in the memory. The memory may be cleared either intentionally by the operator or automatically in a predetermined amount of time.

Third Mode of Presentation

Figure 5:
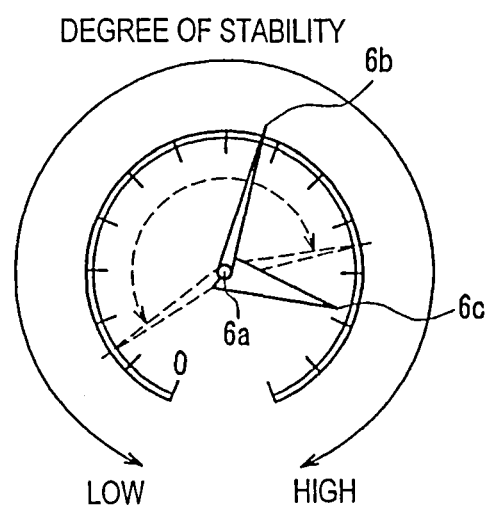
FIG. 5 is another exemplary rating image presenting the degree of stability on an instrument type image.

In this exemplary mode of presentation, the degree of stability of elasticity is presented using an instrument type image as shown in FIG. 5, which illustrates an exemplary instrument type rating image.

As shown in FIG. 5, the instrument type rating image includes pointers 6b and 6c, which turn around the center 6a within a predetermined range. The pointer 6b presents the degree of stability of elasticity. Specifically, the farther the pointer 6b turns clockwise, the higher the degree of stability of elasticity. On the other hand, the farther the pointer 6b goes counterclockwise, the lower the degree of stability of elasticity. In any case, the position of the pointer 6b is determined according to the degree of stability.

Meanwhile, the other pointer 6c indicates the highest degree of stability that has ever been calculated. The methods of calculating and clearing the maximum degree of stability may be just as already described for the second mode of presentation.

As described above, in the second and third modes of presentation, a rating image presenting the degree of stability and another image presenting the maximum degree of stability are both displayed, and therefore, the elasticity can be measured with a target set on the maximum degree of stability. For example, by reference to the maximum degree of stability of elasticity that was obtained in the past by an experienced elasticity monitoring person, even an operator who does not have rich experience in monitoring elasticity can measure the elasticity with a target set on that maximum value. Thus, these types of images can be used effectively in educating trainees to monitor the elasticity properly.

Fourth Mode of Presentation

Figure 6:
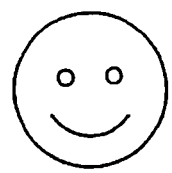
FIG. 6(a) illustrates an image representing a situation where the elasticity has a relatively high degree of stability.
FIG. 6(b) illustrates an image representing a situation where the elasticity has a relatively low degree of stability.
Figure 6:
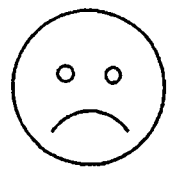

In this exemplary mode of presentation, the degree of stability of elasticity is presented using a round face like image as shown in FIG. 6. Specifically, FIG. 6(a) illustrates how the face like image looks in a situation where the degree of stability of elasticity is relatively high. On the other hand, FIG. 6(b) illustrates how the face looks in a situation where the degree of stability of elasticity is relatively low.

A reference degree of stability has been defined in advance for the stability estimating section 107. The reference value may be entered by the operator using the input device described above.

The stability estimating section 107 compares the degree of stability measured to the reference value. If the degree of stability measured is smaller than the reference value, the stability estimating section 107 may output the data of the image shown in FIG. 6(b) to the image synthesizing section 109. On the other hand, if the degree of stability measured is equal to or greater than the reference value, then the stability estimating section 107 may output the data of the image shown in FIG. 6(a) to the image synthesizing section 109. In the degree of stability display area 111f of the display section 111, one of the two images shown in FIGS. 6(a) and 6(b) is presented.

In this fourth mode of presentation, it can be seen easily whether the degree of stability measured by the stability estimating section 107 exceeds the preset reference value or not. That is why once an experienced elasticity monitoring person has set a reference degree of stability, even an operator who does not have rich experience in measuring elasticity can also see easily if he or she is measuring elasticity with good stability during the measurements.

In the exemplary modes of presentation described above, the degree of stability is presented on the degree of stability display area 111f as shown in any of FIGS. 3 through 6. However, the modes of presentation are not limited to these examples. For example, one of multiple types of images with different colors may be presented according to the degree of stability. Alternatively, one of a number of images in different shapes may be presented according to the degree of stability. For example, a numerical value representing the degree of stability may be presented on the degree of stability display area 111f.

According to this preferred embodiment, the stability estimating section estimates the degree of stability based on the elasticity value and presents an image, or outputs a sound, showing the degree of stability. That is why by sensing a change of sounds emitted from the loudspeaker, for example, the operator can see if he or she is monitoring the subject with stability. In addition, if the degree of stability is presented as a sound, the operator can fix his or her eyes on the image on the monitor. Meanwhile, if a rating image showing the degree of stability is presented on the display section, then the operator can easily see if he or she is monitoring the subject with stability by checking the elasticity distribution or tomographic image on the display section.

Embodiment 2

Hereinafter, a second preferred embodiment of an ultrasonic diagnostic apparatus according to the present invention will be described. The ultrasonic diagnostic apparatus of this preferred embodiment does not present the degree of stability of elasticity on the degree of stability display area 111f but changes the modes of presentation of the tomographic image, elasticity image or electrocardiogram on the display section 111 according to the degree of stability.

For that purpose, the image synthesizing section 109 is notified of the degree of stability by the stability estimating section 107 as shown in FIG. 1 and changes the modes of presentation of the layered image, elasticity image or electrocardiogram, included in the image data, according to the degree of stability. Hereinafter, exemplary images presented on the display section 111 will be described.

First Mode of Presentation

In this exemplary mode of presentation, the degree of stability of elasticity is presented by using the electrocardiogram shown on the biomedical information display area 111e of the display section 111 (see FIG. 3). Hereinafter, such an example will be described with reference to FIGS. 7(a) and 7(b).

Figure 7:
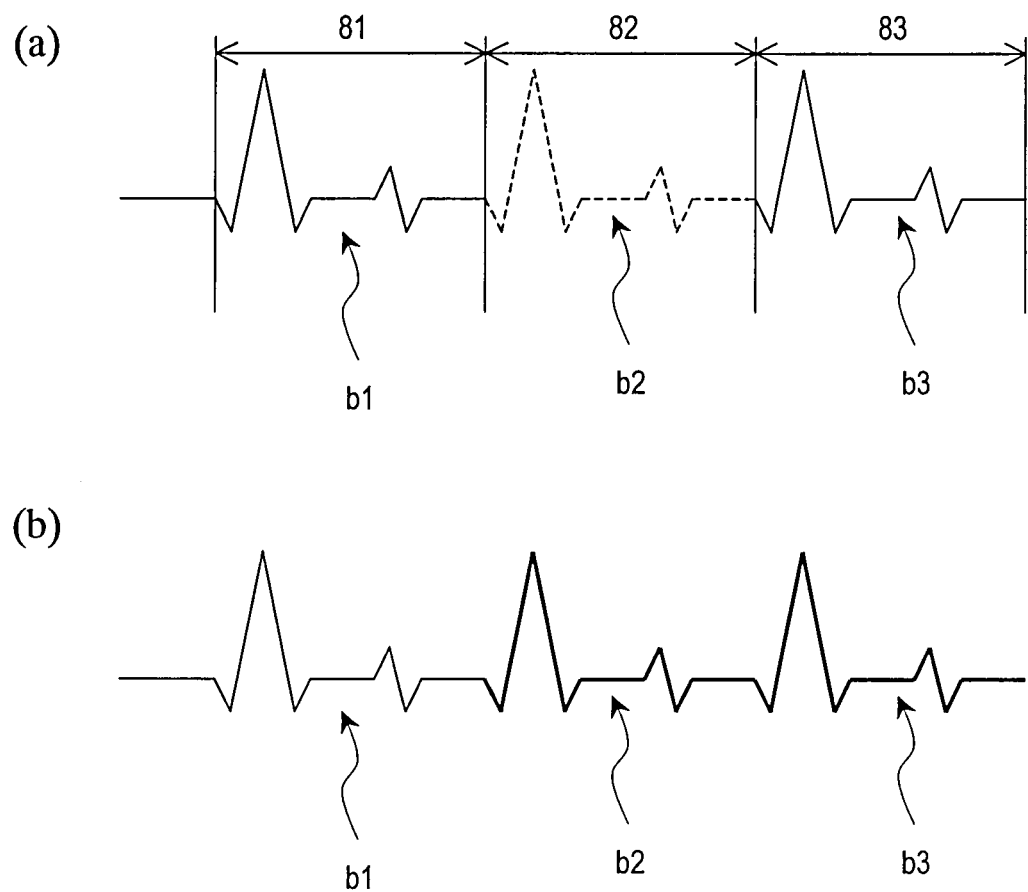
FIGS. 7(a) and 7(b) show two examples of an electrocardiogram that is presented according to the degree of stability.
Figure 8:
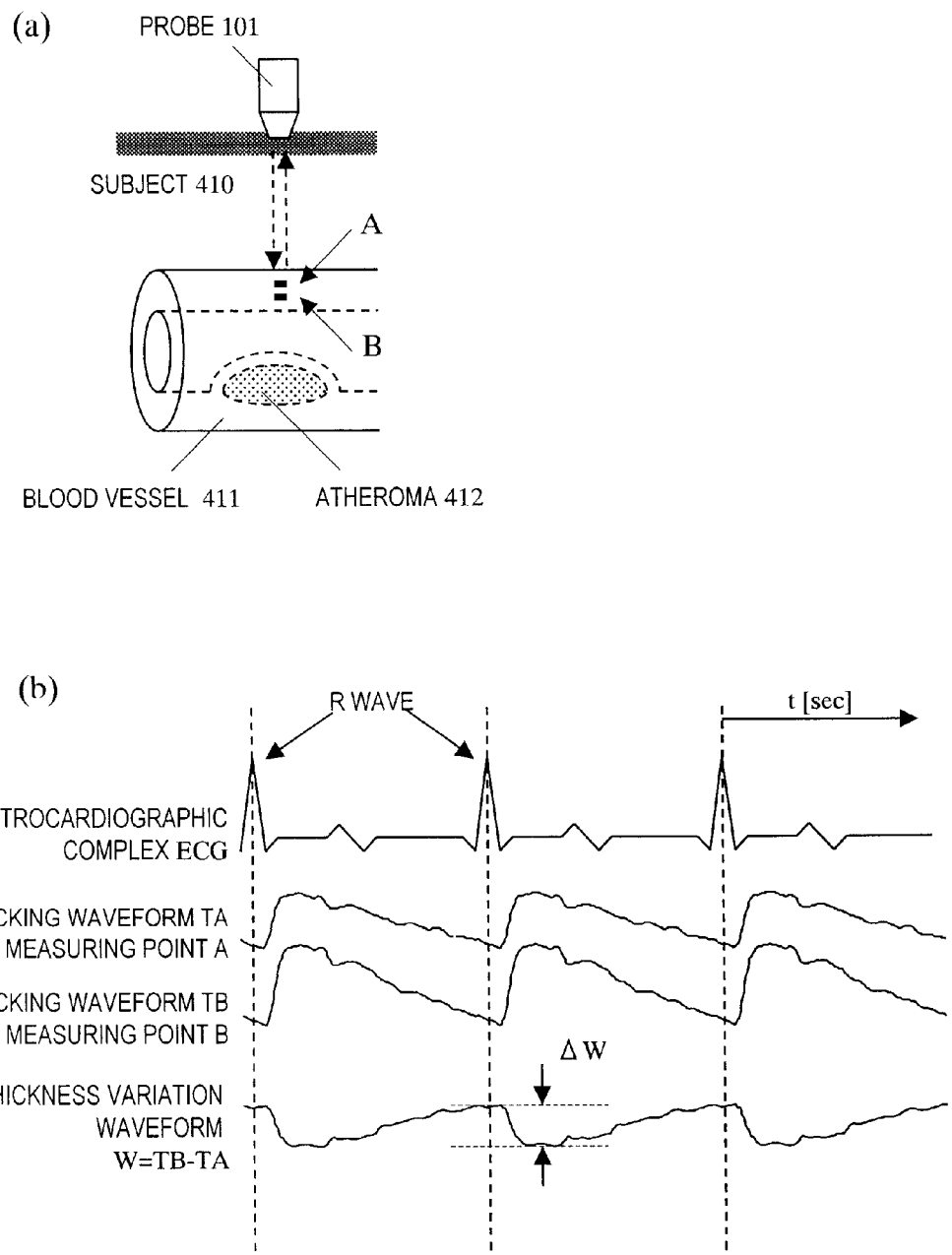
FIG. 8(a) illustrates how a conventional ultrasonic diagnostic apparatus calculates the magnitude of strain based on tracking waveforms of measuring points, which are shown in FIG. 8(b).

FIG. 7(a) shows a subject's electrocardiogram being presented on the biomedical information display area 111e of the display section 111. The portion of the electrocardiogram shown in FIG. 7(a) covers three cardiac cycles b1, b2 and b3. The cardiac cycle b3 shown in the interval 83 is the newest waveform corresponding to one cardiac cycle. That is to say, the electrocardiogram advances from left to right.

The waveform corresponding to one cardiac cycle in the interval 82 is indicated by a dashed curve in FIG. 7(a) but the waveforms in the other intervals are indicated by solid curves. In this case, the solid curves show that the degree of stability of elasticity is relatively high, while the dashed curves show that the degree of stability of elasticity is relatively low.

In the memory of the image synthesizing section 109, a reference degree of stability may be defined in advance. The reference value may be entered by the operator with the input device described above, for example. The image synthesizing section 109 compares the degree of stability supplied from the stability estimating section 107 to the reference value. If the degree of stability is less than the reference value, the image synthesizing section 109 changes the modes of presentation of the electrocardiogram at that point in time into a dashed curve. Since the elasticity and degree of stability are calculated every cardiac cycle, that portion in the dashed curve also corresponds to one cardiac cycle. On the other hand, if the degree of stability is equal to or greater than the reference value, the image synthesizing section 109 changes the modes of presentation of the electrocardiogram at that point in time into a solid curve. As a result, an electrocardiogram including the dashed and solid curves is presented on the biomedical information display area 111e of the display section 111.

Instead of using the dashed and solid curves, the degree of stability may also be presented by the thickness of the curve as shown in FIG. 7(b). Alternatively, the degree of stability of elasticity may also be presented by changing the luminances or color phases of the curve, too.

Optionally, by handling the input device, the operator may set a region of interest (ROI) on the tomographic image 111a. And the degree of stability of elasticity may also be presented by making the image synthesizing section 109 change methods of drawing in terms of the shape, color, luminance or the appearance (i.e., whether it is a dashed curve or a solid curve) of the ROI according to the degree of stability.

Second Mode of Presentation

In this exemplary mode of presentation, the degree of stability of elasticity is presented by using the elasticity distribution shown as the elasticity image 111b on the display section 111. Such an example will be described with reference to FIG. 2.

As shown in FIG. 2, the elasticity image 111b is superimposed on the tomographic image 111a on the display section 111. The degree of stability is presented by the shading of the entire elasticity image 111b.

Hereinafter, a method for changing the luminances of respective pixels of the elasticity image using the luminance IB of the tomographic image, the luminance IE of the elasticity image and a variable k (where 0≤k≤1) that varies proportionally to the degree of stability of elasticity will be described.

The image synthesizing section 109 changes the luminances of respective pixels of the elasticity image with the degree of stability that has been calculated by the stability estimating section 107. For example, using the luminance IB of the tomographic image, the luminance IE of the elasticity image, and a variable k that varies proportionally to the degree of stability of elasticity, the image synthesizing section 109 calculates the luminance IO of the synthetic elasticity image 111b by the following Equation (3):

$$IO = k \cdot IE + (1-k) \cdot IB \quad (3)$$

The image synthesizing section 109 outputs the luminance IO, calculated by Equation (3), as luminance of the respective pixels of the elasticity image 111*b* to the display section 111. As a result, if the degree of stability of elasticity is low (e.g., if k=0), then the elasticity image 111*b* is presented more thinly than the tomographic image 111*a*. On the other hand, if the degree of stability of elasticity is high (e.g., if k=1), then the elasticity image 111*b* is presented more thickly than the tomographic image 111*a*. That is to say, the degree of transparency of the elasticity image 111*b* changes with the degree of stability.

Consequently, if the degree of stability is low, the elasticity image 111*b* has such a high degree of transparency that the tomographic image 111*a* under the elasticity image 111*b* can be seen clearly through the image 111*b*. On the other hand, if the degree of stability is high, the elasticity image 111*b* has such a low degree of transparency (i.e., high degree of opacity) that the tomographic image 111*a* under the elasticity image 111*b* is almost invisible.

It should be noted that the luminance IO of the synthetic image does not have to be calculated by Equation (3). Optionally, only the luminance of the elasticity image 111*b* may be changed with the degree of stability of elasticity without changing the luminance of the tomographic image 111*a*.

As described above, the ultrasonic diagnostic apparatus of this preferred embodiment can present the degree of stability of elasticity by the biomedical information display area or the elasticity image itself without newly creating a degree of stability display area on the display section. That is why there is no need to increase the number of items to present on the display section. In addition, according to the second mode of presentation, the operator can fix his or her eyes only on the elasticity image 111*b*.

Embodiment 3

Hereinafter, a third preferred embodiment of an ultrasonic diagnostic apparatus according to the present invention will be described. In this preferred embodiment, the operator may select a cine mode as the mode of operation of the ultrasonic diagnostic apparatus using the input device. In the cine mode, the apparatus operates just as already described for the first preferred embodiment except that the image data stored in the image memory 110 is continuously output to and presented on the display section 111. Thus, the description of the configuration and the operation of the apparatus will be omitted herein.

In the memory of the image synthesizing section 109, a reference degree of stability may be defined in advance. The reference value may be entered by the operator with the input device, for example. The image synthesizing section 109 receives image output data from the image memory 110 in which the image output data such as the tomographic image and elasticity image is stored. The image output data stored in the image memory 110 is associated with the degree of stability of elasticity that has been calculated by the stability estimating section 107. The image synthesizing section 109 compares the degree of stability of elasticity, associated with the image output data that is stored in the image memory 110, to the reference value. And the image synthesizing section 109 outputs only the image output data, having a higher degree of stability than the reference value, to the display section 111.

By performing such an operation, only image output data with a relatively high degree of stability is selectively presented on the display section 111 among various image output data stored in the image memory 110. That is why the elasticities represented by the images displayed have such small variations that the person monitoring the subject can easily inspect him or her by looking at the tomographic image or elasticity image on the monitor.

According to this preferred embodiment, by classifying the image output data that are going to go to the display section 111 according to the degrees of stability of elasticity that are stored in the image memory 110, it can be seen whether the image output data presented is associated with a high degree of stability or not. Alternatively, the image synthesizing section 109 may sort the image output data, stored in the image memory 110, in the order of magnitudes of stability and then present the data on the display section 111. In this manner, the operator can select only image output data associated with high degrees of stability.

INDUSTRIAL APPLICABILITY

The present invention can be used effectively in an ultrasonic diagnostic apparatus. Among other things, the present invention is applicable particularly effectively to an ultrasonic diagnostic apparatus that calculates a property value of a subject.

The invention claimed is:

1. An ultrasonic diagnostic apparatus comprising;
   a transmitting section, which drives a probe that transmits an ultrasonic wave toward a subject;
   a receiving section, which receives an ultrasonic echo, produced by getting the ultrasonic wave reflected by the subject, through the probe, thereby generating a received signal;
   a tomographic image processing section configured to generate a tomographic image of the subject based on the received signal;
   a property value calculating section configured to calculate property values of the subject at every cardiac cycle of the subject based on the received signal;
   a property value image processing section configured to generate property value images representing the distribution of property values, based on the property values;
   a stability estimating section configured to calculate either the variance or the standard deviation of a plurality of property values that have been calculated in the same spot or region of interest between the property value images of the subject and estimate degrees of stability at the every cardiac cycle of the subject based on the variance or the standard deviation;
   an image synthesizing section, configured to synthesize the tomographic image and the property value image together, thereby generating data for a synthetic image; and
   a display section for presenting the synthetic image and the degrees of stability thereon,
   wherein the image synthesizing section receives the degree of stability from the stability estimating section and changes the modes of presentation of at least one of the tomographic image and the property value image according to the degree of stability.

2. The ultrasonic diagnostic apparatus of claim 1, wherein the stability estimating section further generates rating images representing the degrees of stability and the display section presents the rating images thereon.

3. The ultrasonic diagnostic apparatus of claim 2, wherein the stability estimating section further generates an image representing the maximum value of the degrees of stability that have been calculated sequentially and the display section presents the image representing the maximum value.

4. The ultrasonic diagnostic apparatus of claim 1, wherein the image synthesizing section synthesizes the tomographic image and the property value image together such that corresponding spots of interest agree with each other, and changes the degrees of transparency of the tomographic image or the property value image according to the degree of stability when the two images are superposed one upon the other.

5. The ultrasonic diagnostic apparatus of claim 1, wherein the image synthesizing section receives an electrocardiogram of the subject, synthesizes the electrocardiogram, the tomographic image and the property value image together, and changes the modes of presentation of the electrocardiogram according to the degree of stability.

6. The ultrasonic diagnostic apparatus of claim 5, wherein the mode of presentation of the electrocardiogram according to the degree of stability is changed by employing a dashed electrocardiogram curve or a solid electrocardiogram curve according to the degree of stability.

7. The ultrasonic diagnostic apparatus of claim 5, wherein the mode of presentation of the electrocardiogram according to the degree of stability is changed by changing a thickness of the electrocardiogram according to the degree of stability.

8. The ultrasonic diagnostic apparatus of claim 1, further comprising an input section for defining a region of interest on the tomographic image,
wherein the image synthesizing section changes the modes of presentation of the region of interest on the tomographic image according to the degree of stability.

9. The ultrasonic diagnostic apparatus of claim 1, wherein the image synthesizing section synthesizes the tomographic image and the property val e image together such that corresponding spots of interest agree with each other, and changes the degrees of luminance of the tomographic image or the property value image according to the degree of stability when the two images are superposed one upon the other.

10. The ultrasonic diagnostic apparatus of claim 1, wherein the display section displays the at least one of the tomographic image and the property value image in the synthetic image with different styles of presentation.

11. An ultrasonic diagnostic apparatus comprising:
a transmitting section, which drives a probe that transmits an ultrasonic wave toward a subject;
a receiving section, which receives an ultrasonic echo, produced by getting the ultrasonic wave reflected by the subject, through the probe, thereby generating a received signal;
a property value calculating section configured to calculate property values of the subject at every cardiac cycle of the subject based on the received signal;
a property value image processing section configured to generate property value images representing the distribution of property values, based on the property values
a stability estimating section configured to calculate either the variance or the standard deviation of a plurality of property values that have been calculated in the same spot or region of interest between the property value images of the subject and estimate degrees of stability at the every cardiac cycle of the subject based on the variance or the standard deviation;
a presenting section for presenting the degrees of stability thereon,
wherein the presenting section is an acoustic transducer and transforms an electrical signal, which has been generated based on the degree of stability, into a sound.

* * * * *